United States Patent
Bayston (10) Patent No.: US 10,500,388 B2
(45) Date of Patent: Dec. 10, 2019

(54) MEDICAL DEVICES AND METHODS OF MAKING MEDICAL DEVICES

(75) Inventor: Roger Bayston, Woodthorpe (GB)

(73) Assignee: THE UNIVERSITY OF NOTTINGHAM, Nottingham (GB)

(*) Notice: Subject to any disclaimer, the term of this patent is extended or adjusted under 35 U.S.C. 154(b) by 1576 days.

(21) Appl. No.: 11/690,567

(22) Filed: Mar. 23, 2007

(65) Prior Publication Data

US 2007/0224243 A1 Sep. 27, 2007

Related U.S. Application Data

(63) Continuation of application No. PCT/GB2005/003667, filed on Sep. 22, 2005.

(51) Int. Cl.
| | |
|---|---|
| A61M 39/02 | (2006.01) |
| A61B 17/60 | (2006.01) |
| A61L 27/54 | (2006.01) |
| A61L 29/16 | (2006.01) |
| A61L 31/16 | (2006.01) |

(52) U.S. Cl.
CPC ......... *A61M 39/0247* (2013.01); *A61B 17/60* (2013.01); *A61L 27/54* (2013.01); *A61L 29/16* (2013.01); *A61L 31/16* (2013.01); *A61L 2300/404* (2013.01); *A61L 2300/406* (2013.01); *A61L 2300/45* (2013.01); *A61M 2039/025* (2013.01); *A61M 2039/0285* (2013.01)

(58) Field of Classification Search
None
See application file for complete search history.

(56) References Cited

U.S. PATENT DOCUMENTS

| | | | | |
|---|---|---|---|---|
| 4,917,686 | A * | 4/1990 | Bayston et al. ............... | 604/265 |
| 4,946,444 | A | 8/1990 | Heimke et al. | |
| 5,242,415 | A | 9/1993 | Kantrowitz et al. | |
| 5,624,704 | A * | 4/1997 | Darouiche et al. .......... | 427/2.24 |
| 5,772,640 | A | 6/1998 | Modak et al. | |
| 5,848,992 | A | 12/1998 | Hart et al. | |
| 5,902,283 | A | 5/1999 | Darouiche et al. | |
| 5,906,823 | A * | 5/1999 | Mixon ................... | A01N 25/34 |
| | | | | 424/402 |
| 6,083,208 | A | 7/2000 | Modak et al. | |
| 6,582,719 | B2 * | 6/2003 | Modak et al. ................. | 424/430 |

| | | | | |
|---|---|---|---|---|
| 2001/0010016 | A1 | 7/2001 | Modak et al. | |
| 2003/0153983 | A1 * | 8/2003 | Miller et al. ................. | 623/23.7 |
| 2004/0039349 | A1 | 2/2004 | Modak et al. | |

FOREIGN PATENT DOCUMENTS

| | | |
|---|---|---|
| CA | 2412492 | 12/2002 |
| DE | 199 12 459 A1 | 9/2000 |
| EP | 0 164 896 A | 12/1985 |
| EP | 1 481 697 A1 | 12/2004 |
| JP | 2002-539985 | 11/2002 |
| WO | WO 86/01729 A1 | 3/1986 |
| WO | WO 89/04682 | 6/1989 |
| WO | WO 96/33670 | 10/1996 |
| WO | WO 2003/000243 | 1/2003 |
| WO | WO 03/009879 | 2/2003 |
| WO | WO 03/066119 | 8/2003 |
| WO | WO 03/077866 | 9/2003 |

OTHER PUBLICATIONS

Kim, Charles Y., American Journal of Kidney Diseases, vol. 39, No. 1 (Jan. 2002), pp. 165-173.*
Wu, Weihue, et al., Molecular Medical Microbiology (2015), pp. 1-7. (Year: 2015).*
Bayston, R. et al., "Prevention of hydrocephalus shunt catheter colonisation in vitro by impregnation with antimicrobials," Journal of Neurology, Neurosurgery, and Psychiatry 1989; vol. 52: pp. 605-609.
Wimpenny, J. et al., "Biofilms: The Good, The Bad and The Ugly" published by Bioline for Biofilm Club, fourth meeting of the Biofilm Club, Sep. 18-20, 1999.
Bayston, R. et al., "Mode of action of an antimicrobial biomaterial for use in the hydrocephalus shunts," Journal of Antimicrobial Chemotherapy (2004) vol. 53, pp. 778-782.
European Search Report dated May 27, 2014 in EP Application No. 10178073.
U.S. Appl. No. 15/631,566 (US 2017/0354813), filed Jun. 23, 2017 (Dec. 14, 2017).
International Search Report dated Aug. 24, 2006 in International Application No. PCT/GB2005/003667.

* cited by examiner

*Primary Examiner* — Dennis J Parad
*Assistant Examiner* — Lyndsey M Beckhardt
(74) *Attorney, Agent, or Firm* — Baker Botts L.L.P.

(57) ABSTRACT

A medical device material impregnated with a combination of antimicrobial agents, the combination of antimicrobial agents comprising a first antimicrobial agent, the first antimicrobial agent being triclosan and at least a second antimicrobial agent, wherein the combination of antimicrobial agents provides the device material with antimicrobial activity and inhibition of resistant microbial mutations for of the order of, or greater than, 80 days.

22 Claims, 8 Drawing Sheets

MEDICAL DEVICES AND METHODS OF MAKING MEDICAL DEVICES

CROSS-REFERENCE TO RELATED APPLICATIONS

This application is a continuation of International Application Serial No. PCT/GB2005/003667, filed Sep. 22, 2005, published Mar. 30, 2006, which claims priority from Great Britain Application Serial No. 0421164.5, filed Sep. 23, 2004, each of which are incorporated by reference in their entireties herein, and from which priority is claimed.

This invention relates to medical devices and methods of making medical devices; in particular it relates to implantable medical devices and wound guards. Generally, the implantable medical devices and wound guards are impregnated with one or more antimicrobial agents.

Infection of implantable medical devices (especially partially-implanted devices) is a major concern in healthcare. In the case of central venous catheters (CVC), in the USA, the infection rate is cited as 16% with a direct mortality rate of 25%, usually from generalised sepsis.

There are two main categories of implanted device. Category 1 devices are fully implanted with any catheters etc being tunnelled subcutaneously. Category 2 devices have at least one transdermal portion. Category 2 devices and those Category 1 devices that are accessed transdermally (e.g. through recharging of reservoirs (e.g. ommaya reservoirs) via a hypodermic needle) are therefore much more prone to the introduction of microbes and subsequent infection (Bayston R. Medical Problems due to biofilms. In: Dental Plaque Revisited: Oral Biofilms In Health and Disease; Newman H N, Wilson M, Eds: BioLine, Cardiff 1999).

The causative organisms of such infections comprise fungi (e.g. *Candida* species) *Staphylococcus aureus, Staphylococcus epidermidis, Escherichia coli* and other bacteria Once microbial attachment to the implant has taken place, changes in the microbial phenotype begin which results in a major increase in the amount of antibiotic that is needed to inhibit microbial growth. Implantable devices are infected preferentially by microbes that are able to adhere to the material surface and proliferate in the form of biofilms or the like. Once established, it is known that these biofilm organisms are resistant to antibiotic therapy.

Examples of partially implanted devices that present a risk of infection include wound drains, external ventricular drains, external fixation pins for fracture stabilisation, and voice prostheses. Fracture fixation pins almost always become infected, and while in the majority of cases this is clinically trivial, in a proportion the infection progresses to cause fracture non-union and sometimes osteomyelitis, Devices usually have to be removed in order to eradicate the infection, interrupting vital therapeutic programmes and causing distress, further surgery and further risk to the patient. The degree and consequences of infection vary; for example, all voice prostheses used after a laryngectomy become colonised with *Candida* resulting in poor performance but usually with no general risk to the patient. For aortic vascular grafts the infection rate is 4-8%, but the mortality rate from infection is greater than 50%, with a high risk of limb amputation in the survivors.

An EVD is a device that is used to control cerebrospinal fluid pressure, either after a trauma, or a hemorrhage, or due to a tumour, or in the management of infection. The EVD consists of a catheter that has a portion inside the skull and a portion that exits via a scalp incision to a collection bag via a sterile system. The EVD is a major source of secondary infection by various bacteria, including gram negative strains, during use. This is from two sources: one is the scalp exit site, and the other is the various ports and connectors in the sterile system. For EVDs the infection rate is 12-25%, leading to ventriculitis and sometimes osteomyelitis of the skull, decreased IQ and other serious complications.

Ommaya reservoirs, intraspinal pumps, pacemakers and intra-vascular access devices such as central venous catheters are prone to infection by staphylococci sometimes with dire consequences (for example infection of baclophen intraspinal pumps can give rise to meningitis). Large numbers of these devices have been used worldwide for many years, but the clinical need for the prevention of infection of these devices has never been met.

Grafting of biomaterial into the vascular system is a very common treatment, particularly for patients over fifty years of age. Grafting can be carried out on a peripheral vessel, a cardiac vessel or one of the major vessels such as the aorta. Grafts are made from Dacron or PTFE fabric and are sealed with gelatin or collagen. Grafts that are particularly at risk of infection are abdominal aortic grafts, especially with groin incision. The pathogenesis of the infection of these devices is not clearly understood, but one of the most serious forms is infection of the perigraft space, usually with *S aureus* but sometimes with pseudomonas and other gram negative bacteria. Infection rates vary but are about 4-8% in this site. However the mortality rate can be as high as 50% of those infected, due to graft disruption and rapid exsanguination.

Wound guards are used to protect the entry point of a transdermal device into the skin. Important examples of transdermal devices include central venous catheters, external ventricular drainage catheters, catheters for delivery of continuous ambulatory peritoneal dialysis (CAPD), and external fixation pins for fracture stabilisation.

A prior art wound guard consists of a polyurethane foam disc impregnated with the antimicrobial agent chlorhexidine. A disadvantage of this wound guard is that it requires adhesive tape to fix it to the skin and the foam disc absorbs serous fluid making the wound guard floppy. Because of these problems it is necessary to change the wound guard frequently. The wound guard may swell as it absorbs serous fluid and can become difficult to handle.

It is known that medical devices can be rendered antimicrobial by coating them with an antibiotic or antimicrobial substance. A major disadvantage of a coated implant is that when exposed to flow conditions, such as in the vascular system, the antibiotic substance readily leaches from the implanted device into the surrounding environment e.g. into the blood of a patient, with loss of activity (Braithwaite B D, Davies B, Heather B P, Earnshaw J J, 'Early results of a randomised trial of rifampin—bonded grafts for extra—anatomic vascular reconstruction' Joint Vascular Research Group; Br J Surg 1998, 85: 1378-1381. Jansen B, Jansen S, Peters G, Pulverer G, 'In vitro efficacy of a central venous catheter (hydrocath) loaded with teicoplanin to prevent bacterial colonisation' J Hosp Infection 1992, 22: 93-107; Bach A, Darby D, Böttiger B, Böhrer H, Motsch J, Martin E, 'Retention of the antibiotic teicoplanin on a hydromer—coated central venous catheter to prevent bacterial colonisation in postoperative surgical patients', Intensive Care med. 1996, 22, 1066-1069).

Further disadvantages include the implantable device becoming coated with a host-derived conditioning film consisting of glycoproteins and other substances, which inactivate or obliterate the antimicrobial coating. If the antimicrobial coating is of a metal in elemental or salt form, the metal or salt becomes bound to host-derived proteins and subsequently inactivated. All these processes result in a rapid loss of antimicrobial protection of the device.

PCT patent application WO 03/066119 describes a method of making an insertable device in which an antimicrobial agent is mixed with a matrix polymer to form a homogeneous mixture which is then shaped to form part of the insertable device. Antimicrobial agents that are mixed with a polymer, e.g. in the form of a powder, suffer from the problem that there is a limit as to how much of the powder that can be added to the polymer before impairment of the mechanical properties of the device that would prevent the proper functioning of the device. This limits the amount of antimicrobial agent that can be added to the polymer and therefore the length of time that a device made with such a polymer is resistant to microbial infection. If an antimicrobial agent so 'impregnated' (correctly termed 'admixed') is not evenly dispersed in the matrix this may cause problems with rapid leaching of the antimicrobial agent from the matrix and less than ideal release properties.

PCT patent application WO 03/009879 describes medical devices, such as ureteral stents and urethral catheters, that have a polymer matrix containing an antimicrobial agent and a surfactant region disposed over the polymer matrix. The surface properties of the device are affected by the surfactant and the formation of a biofilm on the device is inhibited. Similarly, PCT patent application WO 03/066119 describes medical devices that comprise a polymer region having an antimicrobial agent and a biofilm inhibitor. The medical device is formed by mixing the antimicrobial agent with a polymer melt and then shaping the polymer to form the device. In this application the medical devices generally provide drainage between two sterile areas of the body or between a sterile or non-sterile area of the body. WO 03/009879 and WO 03/066119 describe devices that can be used in the body for long periods of times without infection. Such long-term use may be due to the fact that the devices used do not have a transdermal portion (e.g. category 1 devices) and therefore are not subject to continual exposure to bacteria, and in particular resistant strains of bacteria from outside the body.

U.S. Pat. No. 5,902,283 describes a method of impregnating a non-metallic medical implant comprising the steps of forming an antimicrobial composition by dissolving an antimicrobial agent in an organic solvent, adding a penetration agent to the composition and applying the antimicrobial composition to the medical implant. The antimicrobial agents used include a mixture of minocycline and rifampin. When these agents where used to impregnate a coated 7-fr polyurethane vascular catheter the duration of efficacy against *Staphylococcus epidermidis* was between 45 and 60 days. Impregnated catheters were tested by suspending the catheters in human urine for 7 days and a zone of inhibition of 10 mm or greater was used as a test to indicate antimicrobial efficacy.

Triclosan (available from Ciba Specialty Chemical Products under the trade name Irgasan DP300) is an antimicrobial agent that is commonly used in cosmetics, lotions and hand soaps. It is also used as an additive to plastics and polymers to make food packaging. It is not commonly used to give implanted medical devices antimicrobial activity. However, U.S. Pat. No. 5,772,640 describes the use of triclosan in combination with chlorhexidine in an impregnated device. Kim et al. also describe the use of triclosan for impregnated devices (Kim C Y, Kumar A, Sampath L, Modak S. 'Evaluation of antimicrobial—impregnated continuous ambulatory peritoneal dialysis catheter for infection control in rats', Amer J Kidney Diseases 2002, 39: 165-173). In this case triclosan was added as a powder to a liquid polymer before forming the medical device. Only a small quantity of the triclosan could be added in this way before the triclosan had a detrimental effect on the mechanical properties of the formed medical device.

The lack of structural integrity in some impregnated medical devices and the rapid dissolution of antimicrobial agents in coated medical devices means that there remains a need to prevent infection associated with implanted medical devices, in particular for Category 2 implanted devices, i.e. those partially implanted in the body. These devices often have a transdermal portion, therefore there is a risk of infection from the environment and other sources (e.g. the patient's skin surfaces, contaminated fluids, operators' hands etc) throughout the duration of the use of the device.

The incidence of infection of implanted medical devices directly impairs patient treatment and is compounded by the need to replace such medical devices following infection. The use of the current invention will reduce the incidence of infection dramatically and thus will significantly reduce the need of replacement of those medical devices making use of the invention.

A first aspect of the invention provides a medical device material impregnated with a combination of antimicrobial agents, the combination of antimicrobial agents comprising a first antimicrobial agent, the first antimicrobial agent being triclosan and at least a second antimicrobial agent, wherein the combination of antimicrobial agents provides the device with antimicrobial activity and inhibition of resistant microbial mutations for of the order of, or greater than, 80 days.

Preferably, the combination of antimicrobial agents provides the device with antimicrobial activity and inhibition of resistant mutants from both gram positive and gram negative bacteria. Therefore the device exhibits antimicrobial activity against and prevents the appearance of resistant mutant strains in a broad spectrum of microbes. In particular the device will exhibit antimicrobial activity against and prevent the appearance of resistant mutant strains in the gram-negative bacteria *Escherichia coli* and the gram-positive bacteria *Staphylococcus aureus*.

The invention therefore provides the technical effect, and benefit, that by impregnating a medical device with a combination of antimicrobial agents that includes triclosan it is not necessary to remove the medical device from a patient (to clean or replace the device) for a clinically significant period of time.

Importantly, when triclosan is included in a combination of antimicrobial agents, for example with rifampin and clindamycin, the length of time that it is possible to maintain antimicrobial activity and prevent the growth of resistant mutant strains can be longer than 190 days.

Although triclosan has antimicrobial activity for greater than 190 days against a wide spectrum of microbes it is possible, over this period of time, for microbes to mutate into a strain that is resistant to triclosan. The presence of a second antimicrobial agent will generally be bactericidal or bacteriostatic to the mutant strain. Of course a microbe that mutates to be resistant to the second antimicrobial agent will be generally be killed by the triclosan. A microbe strain will survive the presence of the two antimicrobial agents only in the case when a strain is produced by a single mutation (or two mutations that occur within a short period of time) that is resistant to both triclosan and the second antimicrobial agent. When two antimicrobial agents have different modes of action to prevent microbial growth the probability of such a single mutation affecting both modes is very low as can be calculated from the mutation frequencies of the organisms concerned. However, the polymeric material of the device may be impregnated with a third antimicrobial agent which has a different mode of action or target than the other two antimicrobial compounds. A single mutation (or three mutations that occur within a short period of time) would need to produce a strain that is resistant to all three of the antimicrobial agents.

Hence, according to an embodiment of the invention the second antimicrobial agent has a different mode of action to triclosan. The primary mode of action of triclosan is the blocking of acyl carrier protein (ACP) reductase (Fab1) that is essential in bacterial fatty acid synthesis. A secondary mode of action is thought to be damage to the bacterial cell membrane, causing electrolyte leakage.

In one example the mode of action of the second antimicrobial agent is the blocking of protein synthesis. Such a mode of action may be provided by lincomycin or a derivative thereof such as clindamycin. In another example the mode of action is the interference with the synthesis of RNA. Such a mode of action may be provided by rifamycin or a derivative thereof such as rifampin.

In an embodiment of the invention the polymeric material is impregnated with a third antimicrobial agent, wherein if the second antimicrobial agent is lincomycin, or a derivative thereof such as clindamycin, then the third antimicrobial agent is rifamycin, or a derivative thereof such as rifampin, whereas if the second antimicrobial agent is rifamycin or derivative thereof such as rifampin then the third antimicrobial agent is lincomycin or a derivative thereof, such as clindamycin.

In a further embodiment of the invention trimethoprim, a lincosamine, a quinolone, a tetracycline or a glycylcyclines can act as a replacement antimicrobial agent for clindamycin, that is, any one of these agents may be used in combination with triclosan and a rifamycin.

In another embodiment of the invention the trimethoprim and quinolone are used in combination with triclosan.

The long activity and inhibition of resistant mutant strains provided by the combination of antimicrobial agents embodied by the invention could not have been readily predicted from trials of other combinations of antimicrobial agents. For example, it will be shown that the combination of rifampin with clindamycin exhibits activity and inhibition of resistant mutant strains for the order of 70 days whereas when triclosan is included in this combination of antimicrobial agents the period of activity/inhibition exceeds 190 days. The inhibition to resistant mutant strains provided in the period 70 to 190 days would not be expected because the combination of rifampin and clindamycin will have lost growth-inhibitory activity as determined by a zone plate after about 70 days. Therefore the combination of triclosan with rifampin and/or clindamycin provides a surprising effect.

This step-change in longevity of antimicrobial protection may be as a result of an interaction of triclosan with the other antimicrobial agents or the effect of triclosan to make bacteria more susceptible to low levels of antibiotics, perhaps by acting to reduce their viability.

Preferably the combination of antimicrobial agents provides the device with antimicrobial activity and inhibition of resistant microbial mutations for the order of, or greater than, one of 90 days; 100 days; 120 days; 140 days; 160 days; and 190 days.

An embodiment of the invention provides a medical device comprising the medical device material of the first aspect of the invention.

It should be understood that for the purposes of this disclosure the term "medical device" covers both a component of a medical device and the entire medical device.

The antimicrobial activity of a medical device embodying the invention provides a significant step-wise improvement over existing impregnated medical devices which to date have achieved only 45 to 60 days (Bayston R, Grove N, Siegel J, Lawellin D, Barsham S. Prevention of hydrocephalus shunt catheter colonisation in vitro by impregnation with antimicrobials. J Neurol Neurosurg Psychiatr 1989, 52: 605-689; Bayston R, Lambert E. Duration of protective activity of cerebrospinal fluid).

In this application "antimicrobial activity" is defined as the ability of a medical device to create a zone of inhibition of microbial growth of an index bacterium, typically a clinical isolate, around the medical device or portion thereof in microbiological assays A zone of inhibition is a zone in which no microbial growth is evident as assessed by the naked eye. For a serial plate transfer test (described later in this application) the zone of inhibition will generally extend to a width of at least 1 mm (but often as much as 35 mm or even more) beyond the boundary of the test material placed on the surface of a nutrient (agar) medium, however, the ability of the test material to inhibit microbial growth beneath the test material is also taken into account (i.e. a zone of inhibition may be observed beneath the test material).

"Inhibition of resistant mutant strains" is a very different measure and in this application is to be taken to mean the absence of any visible bacterial colonies in any zone of inhibition.

The length of time that antimicrobial activity and inhibition of resistant microbial mutations is exhibited depends on the geometry of the device that has been impregnated with the combination of antimicrobial agents. The greater the ratio of volume to surface area exposed to antimicrobial removal or leaching of the device, the greater the period that antimicrobial activity and inhibition of resistant microbial mutations is exhibited. For example silicone wound guards comprising a disc of 2.5 cm diameter and 3.5 mm thickness showed antimicrobial activity and inhibition of resistant microbial mutations for greater than 190 days. However intra-vascular devices (such as catheters or intravenous lines) may show such activity/inhibition for a shorter time.

There are many methods for determination of antimicrobial activity. A suitable method is the serial plate transfer test (SPTT) (Bayston R. Grove N, Siegel J, Lawellin D, Barsham S. Prevention of hydrocephalus shunt catheter colonisation in vitro by impregnation with antimicrobials. J Neurol Neurosurg Psychiatr 1989, 52: 605-689) which allows for a portion of an antimicrobial material, typically a catheter segment of approximately 5 mm length, to be placed on the surface of an agar plate seeded with susceptible index bacteria in such a way that the cut ends of the test catheter are not in contact with the eluting surface, by means of a well or other arrangement. After incubation the zone of inhibition is measured, and the segment transferred to a second plate and the process repeated until no zone of inhibition is apparent. The SPTT is a reputable test which is an improvement on the simple zone plate test as it provides data not only on antimicrobial activity but also on duration of antimicrobial activity.

Tests can also be carried out on assays to determine the time taken to kill 100% of adhered bacteria—so called "tK100" tests (Bayston R, Ashraf W, Bhundia C., Mode of action of an antimicrobial biomaterial for use in hydrocephalus shunts, J. Antimicrobial Chemotherapy (2004) 53, 778-782).

Rifampin and clindamycin have no activity against *E. coli* but triclosan does. Interestingly, the combination of all three provides both antimicrobial activity against *E. coli* for over 190 days and also prevents the appearance of resistant mutant strains of *E. coli* for over 190 days. Thus giving real utility to the invention. Again, this is not predictable from the prior art. Triclosan when used alone provides antimicrobial activity for 190 days but does not prevent the appearance of resistant colonies.

A second aspect of the invention provides a medical device material impregnated with a combination of antimicrobial agents, the combination of antimicrobial agents comprising a first antimicrobial agent, the first antimicrobial agent being triclosan a second antimicrobial agent and a third antimicrobial agent, wherein the combination of antimicrobial agents provides the device with antimicrobial activity and inhibition of resistant microbial mutations for of the order of, or greater than, 80 days.

It will be appreciated that the embodiments described with reference to the first aspect of the invention are applicable to the second aspect and other aspects of the invention.

Preferably the second antimicrobial agent is rifampin and the third antimicrobial agent is clindamycin.

Classes of antibiotics that could possibly be used as the second or third antimicrobial agent include tetracyclines (e.g. minocycline), rifamycins (e.g. rifampin), macrolides (e.g. erythromycin), penicillins (e.g. nafcillin), cephalosporins (e.g. cefazolin), other beta-lactam antibiotics (i.e. imipenem, aztreonam), aminoglycosides (e.g. gentamicin), chloramphenicol, sulfonamides (e. sulfamethoxazole), glycopeptides (e.g. vancomycin), quinolones (e.g. ciprofloxacin), fusidic acid, metronidazole, mupirocin, polyenes (e.g. amphotericin B), azoles (e.g. fluconazole), beta-lactam inhibitors (e.g. sulbactam) and oxazolidinones (e.g. linezolid)).

Examples of specific antibiotics that can be used include minocycline, erythromycin, nafcillin, cefazolin, imipenem, aztreonam, gentamicin, sulfamethoxazole, vancomycin, ciprofloxacin, trimethoprim, metronidazole, teicoplanin, mupirocin, azithromycin, clarithromycin, ofloxacin, lomefloxacin, norfloxacin, nalidixic acid, sparfloxacin, pefloxacin, amifloxacin, enoxacin, fleroxacin, temafloxacin, tosufloxacin, clinafloxacin, sulbactam, clavulanic acid, amphotericin B, fluconazole, itraconazole, ketoconazole, linezolid and nystatin.

Examples of antiseptics and disinfectants that could be used as the second or third antimicrobial agent are hexahlorophene, cationic bisiguanides, iodine and iodophores (e.g. povidone-iodine), para-chloro-meta-xylenol, furan medical preparations (e.g. nitrofurantoin and nitrofurazone), methenamine, aldehydes (e.g. glutaraldehyde and formaldehyde) and alcohols.

A third aspect of the invention provides a method of making a medical device, comprising: forming a medical device from polymeric material; impregnating the formed medical device with a solution of a swelling agent and a first antimicrobial agent, the first antimicrobial agent being triclosan; allowing the solution of the swelling agent and triclosan to penetrate the formed medical device; removing the swelling agent from the medical device or component to leave triclosan impregnated in the medical device.

The method of the third aspect of the invention allows a relatively large quantity of the triclosan to be incorporated into the elastomeric material without deterioration of the mechanical properties of the polymeric material to an extent which would lead to the polymeric material being unfit for use in the medical device. The triclosan can have a concentration of up to 1000 mg/litre in the swelling agent which can result with a concentration of between 0.1% and 3% w/w in the polymeric material.

The method of the third aspect of the invention can also be used to impregnate a medical device with other antimicrobial agents in combination with triclosan (e.g. clindamycin and/or rifampin in combination with triclosan).

The polymeric material may be material chosen from silicone elastomer, polyolefins (polyalkenes), PTFE, Dacron™ (polyethylene terephthalate polyvinyl chloride), silicone polyeurethane copolymer and polyurethane latex. Silicone elastomer is preferred because it has good mechanical properties (e.g. it is flexible and resilient to tears), does not absorb bodily fluids (e.g. plasma, blood, CSF), has good heat resistance and can be produced so that it is substantially transparent. This is in contrast to other materials such as foamed polymers (e.g., polyurethane foam) that, whilst being flexible, are inherently absorbent, opaque and susceptible to tearing.

The swelling agent is chosen from hexane, toluene, xylene, chloroform, an ester, a ketone and methylene chloride and may be a mixture of two or more such agents. Preferably, the swelling agent is chloroform.

After the swelling agent has been removed from the polymeric material the polymeric material returns to, or near to, its original size. At this stage it is preferable to autoclave the medical device. This has the effect of sterilising the medical device. Autoclaving also has a beneficial effect on the diffusion characteristics of the antimicrobial agent into the polymeric material by increasing the crosslinking density of the polymeric material. Thus the increased crosslinking density compared to that pertaining during impregnation provides a diffusion rate-limiting mechanism.

A variation of the third aspect of the invention is to impregnate polymeric material, which has not yet been formed into a medical device, and then form the medical device into the required shape after impregnation.

The method of the third aspect of the invention is particularly advantageous when the method is use to impregnate a medical device which is one of the following: a wound guard, an external ventricular drainage device, an ommaya reservoir, a intraspinal pump, a stent (for example, but not limited to, arterial stents, including coronary artery stents), a central venous catheter, an ascites shunt, a pacemaker, a continuous ambulatory peritoneal catheter, a voice prosthesis, a vascular graft, a urinary catheter, and an intraocular lens. These devices represent devices where there is a high risk of infection and/or severe consequences from infection (such as mortality or disability) and where conventional methods of reducing infection have not been very successful.

An embodiment of the invention comprises impregnating a Dacron or PTFE vascular graft with an antimicrobial agent. The common approach to prevent vascular graft infection is to treat the gelatin seal of the graft immediately before use by soaking the graft with an aqueous solution of rifampin. However recent studies (Earnshaw J J. The current role of rifampicin-impregnated grafts: Pragmatism Versus Science. European Journal of Vascular & Endovascular Surgery. 20(5) 409-412, 2000) have shown that this technique makes no significant difference to the infection rate, probably due to the rapid removal of the rifampin by blood flow and its obliteration by plasma proteins. This embodiment of the invention impregnates the graft itself, rather than the seal.

A fourth aspect of the invention provides a wound guard having a first surface for contacting the surface of the skin of a patient and a second surface disposed away from the first surface, and a projection which projects away from the second surface of the disc portion, wherein said projection has a bore passing through the projection to said first surface, said projection being adapted to hold a transdermal device, in use, in said bore.

Preferably the first and second surfaces of the wound guard define in part a disc having a perimeter that forms an annule, however other shapes could be used The projection may, in use, provide lateral support for the transdermal device. The projection may, in use, grip the transdermal device.

According to a fifth aspect of the invention there is provided a wound guard comprising a contact surface for contacting the surface of the skin of a patient and a second surface disposed away from the contact surface, and a projection which projects away from the second surface of the disc portion, wherein said projection has a bore passing through the projection to said first surface, said projection holding a transdermal device in said bore.

The projection provides extra support for the transdermal device and increased frictional resistance to movement of the transdermal device within the bore. This can stabilise the transdermal device so that it is more stable against both axial movement and transverse movement to the axial direction, thereby reducing the risk of pain and damage to a patient by accidental movement of the transdermal device.

The wound guard is suitable for holding a range of transdermal devices such as central venous catheters, continuous ambulatory peritoneal dialysis catheters, external ventricular drains, and external fixation pins and screws for fracture stabilisation, and catheters for wound drains.

Preferably, the disc portion is composed of polymeric material. More preferably, the projection is also composed of polymeric material. Conveniently the disc portion and the projection are integrally formed. The disc portion and/or the projection may comprise one or more antimicrobial agents.

A sixth aspect of the invention provides a wound guard having a contact surface for contacting the surface of the skin of a patient, and a bore passing through the wound guard for holding a transdermal device, the wound guard being composed substantially of a polymer material chosen from silicone elastomer, rubber and polyurethane latex.

A wound guard composed of a polymeric material such as silicone elastomer has a high mechanical strength, for example it is resistant to tears. Such a wound guard is not adversely affected by water or other fluid such as blood and plasma and, unlike prior art polyurethane foam wound guards, the wound guard of the invention retains its mechanical strength when in a wet or damp environment. The wound guard may be removed from the wound site, washed and replaced at the wound site by virtue of having a radial slit. The patient may also be able to take a shower or bathe without the need to remove or replace the wound guard.

A wound guard made of a polymer with elastic properties (e.g. a silicone elastomer) such that the bore of the wound guard grips the transdermal device will help to fix the wound guard on to the wound without the need for adhesive between the underside of the wound guard and the skin surrounding the wound. Preferably, the polymeric material is impregnated with a first antimicrobial agent. Preferably, the first antimicrobial agent is triclosan so that the polymeric material is provided with antimicrobial activity for of the order of, or greater than: 80 days; 120 days; or 190 days.

Preferably, the polymeric material is impregnated with a second antimicrobial agent, so that the polymeric material is provided with antimicrobial activity and with the ability to prevent the appearance of resistant mutant bacterial strains for of the order of, or greater than: 80 days; 120 days; or 190 days. More preferably the polymeric material is impregnated with a third antimicrobial agent.

According to a seventh aspect of the invention there is provided a wound guard comprising a first surface for contacting the skin of a patient and a second surface disposed away from the first surface, and a bore passing through the wound guard for holding an object that penetrates the skin, the wound guard being impregnated with a first and second antimicrobial agent, so that the wound guard is provided with antimicrobial activity and with the ability to prevent the appearance of resistant mutant bacterial strains.

In an embodiment of the invention the wound guard has a radial slit to allow easy application to and/or removal of the wound guard from a transdermal device.

According to an embodiment of the invention there is provided a method of treating a patient comprising using a medical device material or medical device in accordance with the first or second aspects of the invention, or a wound guard in accordance with the fourth, fifth, sixth or seventh aspects of the invention.

An eighth aspect of the invention provides a method of making a medical device or a component of a medical device, comprising: impregnating a first portion of the medical device or component with a first antimicrobial agent; impregnating a second portion of the medical device or component with a second antimicrobial agent, the second portion being distinct from the first portion; and treating one or both of the first and second portions so that the medical device has a portion that has both the first and second antimicrobial agents.

The portion that has both the first and second antimicrobial agents may be the first portion and/or the second portion or it may be a portion that is distinct from both the first portion and the second portion.

The treating step may comprise applying heat to at least part of at least one of the first and second portions. Preferably, the treating step comprises autoclaving of the medical device since this has the added effect of sterilising the device.

The impregnating steps may occur with the first and second portions being separate from each other (e.g. in separate pieces of material) and the treating step occurs with the first and second portions being in contact with each other. Therefore, it is possible for the first portion to be impregnated with the first antimicrobial agent using a first technique and the second portion to be impregnated with the second antimicrobial agent using a second, different, technique. For example, the first technique may comprise the method of the second aspect of the invention, and the second technique may comprise impregnating the second antimicrobial agent into the second portion with a solution, emulsion or suspension of the second antimicrobial agent in a supercritical fluid. In this way the second technique will not destroy or degrade the first antimicrobial agent since the first antimicrobial agent is never exposed to the second technique.

Embodiments of the invention will now be described in more detail by way of example with reference to the accompanying drawings, of which.

Figure 1:
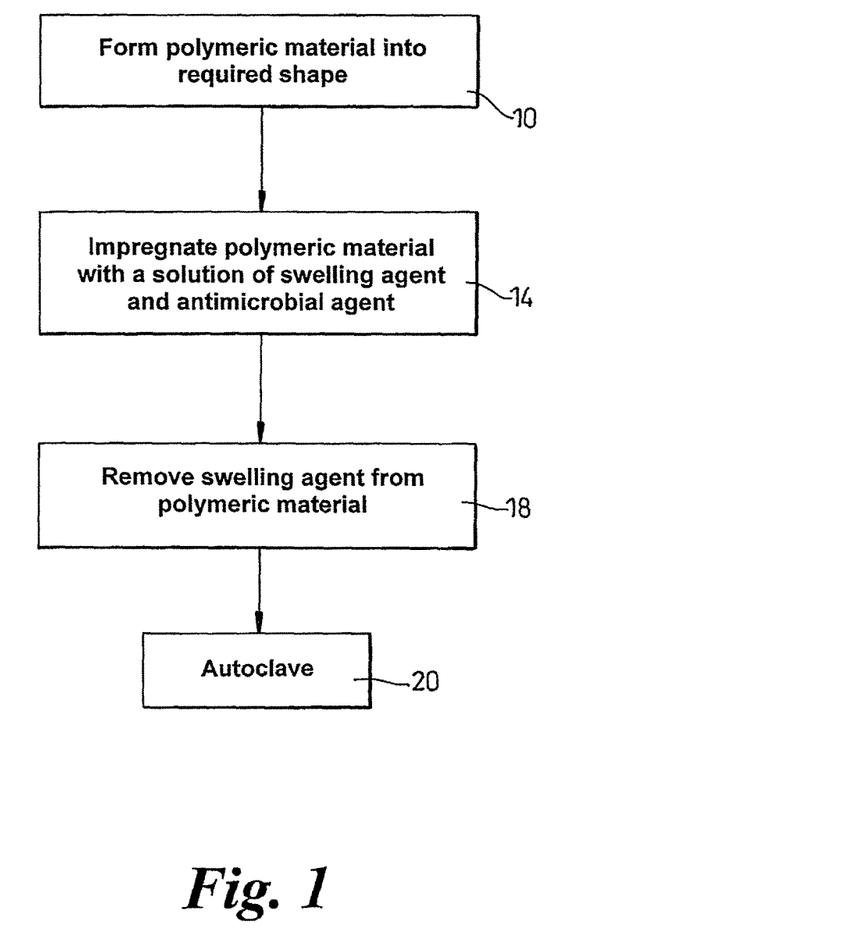
FIG. 1 schematically illustrates a method for impregnating polymeric material with an antimicrobial agent.

Following an aspect of the invention a medical device is impregnated with triclosan and at least one other antimicrobial agent. Referring to FIG. 1, at step 10 a medical device is formed from a polymeric material such as a silicone elastomer or the like. The silicone elastomer may form a capsule that encloses part of or all of the rest of the device for example the silicone elastomer may encapsulate a pacemaker. The silicone elastomer may form the entirety of the medical device, for example a wound guard (as will be described later) or a portion of a medical device, such as a catheter, that is joined to the rest of the device. In any case the polymeric material is formed into the shape that is required for the medical device.

At step 14 the formed polymeric material is placed in a solution of a swelling agent, preferably chloroform, and one or more antimicrobial agents. The polymeric material is left in the solution to enable penetration and swelling of the polymeric material. The swelling caused by enlarged intermolecular spaces in the polymeric material allows substantial homogeneous dispersion of the antimicrobial agent(s) throughout the body of the polymeric material.

The ability of an antimicrobial agent to impregnate the polymeric material is indicated quantitatively by the solubility of the agent in a solvent (for example, chloroform, hexane or toluene) in which the polymer is also soluble.

Antimicrobial agents that are particular suitable include clindamycin hydrochloride, trimethoprim and rifampin which is a semi-synthetic antibiotic derivative of rifamycin B (specifically, rifampin is the hydrazone, 2-(4-methyl-1-piperazinyl-iminomethyl)-rifamycin SV). Clindamycin, trimethoprim and rifampin, when dissolved in the swelling agent, provide greater penetration into the elastomer compared to other antimicrobial agents. Triclosan is also able to penetrate the polymeric material and triclosan is used as one of the antimicrobial agents because it has a long antimicrobial activity against a broad spectrum of microbes (covering both gram positive and gram negative bacteria) and in combination with rifampin and/or clindamycin provides protection against the appearance of resistant mutant bacterial strains for as much as 190 days. Preferably the concentration of the antimicrobial agent(s) is 0.1% to 0.2% by weight of each agent to the volume of the swelling agent. For rifampin and clindamycin this results in concentrations in the polymer of typically 0.05 mg/g and 0.16 mg/g respectively. Higher percentages of the antimicrobial agent(s) in the swelling agent such as 1% or as much as 2% or even 3% could also be used.

At step 18 the swelling agent is removed from contact with the polymeric material, for example by removing the polymeric material from the solution, draining the solution from the polymeric material and allowing the swelling agent to evaporate from the polymeric material. The swelling of the polymeric material is thereby reversed and the polymeric material returns to, or close to, its original shape and size.

At step 20, after the swelling agent is removed from the polymeric material, the polymeric material is sterilised by autoclaving. Sterilisation may also be achieved by using ethylene oxide or gamma radiation. Autoclaving is preferred because this method has a beneficial effect on the diffusion characteristics of the antimicrobial agent into the polymeric material by increasing the crosslinking density of the polymeric material. Preferably the autoclaving is at a temperature of about 121° C. and a pressure of about 15 psi ($1.03 \times 10^5$ N/m$^2$) for about 20 minutes. The pressure, temperature and duration of the autoclaving may be varied in accordance to the size, shape and other characteristics of the device and the overall load in the autoclave to achieve complete sterilisation. Another reason for preferring autoclaving for the sterilisation process is that ethylene oxide is known to interact with some antimicrobial agents, e.g. rifampin, with which it produces potentially harmful oxidation products. Gamma radiation is unsuitable for sterilisation of some implantable polymers because it causes surface damage to the polymer.

A method of impregnating a polymeric substance with an antimicrobial agent, when the agent is a metal, metal salt, or metal complex is by impregnating the substrate with a solution, emulsion or suspension of the antimicrobial agent in a supercritical fluid (e.g. supercritical carbon dioxide). WO 03/045448 describes such a method and is herein incorporated by reference. Metals are generally not soluble in supercritical fluids therefore it is necessary for the metal to form part of a chelated complex, the chelated complex being soluble in the supercritical fluid. Such a complex will generally be an organometallic complex. The polymeric material is then impregnated with the solution of the chelated complex. After impregnation the polymeric material is exposed to hydrogen gas which reduces the complex causing the complex to decompose to leave metal atoms in the polymeric material. The metal atoms aggregate to form metal particles in the polymer matrix. This method can be used with the method described in reference to FIG. 1 to impregnate a medical device both with triclosan (and possibly with one or more other organic antimicrobial agents) and a metal/metal salt/metal complex.

The results of various tests using polymeric material impregnated with one or more antimicrobial agents are presented below. The impregnation was achieved using the method illustrated in FIG. 1.

Simulation of Protection of Exit Site

Wound guards (e.g. for protection of catheter or external fixation pin exit sites) in the form of discs of silicone elastomer of 2.5 cm diameter and 3.5 mm thickness were impregnated with either rifampin+clindamycin (A), rifampin+clindamycin+triclosan (B) or triclosan alone (C). The discs were then sterilised by autoclaving, and placed on agar plates seeded with the gram-positive bacteria *Staphylococcus aureus*. After overnight incubation, inhibition zones were measured and the discs were transferred to a further seeded plate, and this process repeated until no zones were seen. Any bacterial colonies growing inside the inhibition zones or under the discs were tested for minimal inhibitory concentration (MIC) to triclosan and their identities with the original inoculum determined by pulse field gel electrophoresis. The results were as follows:

TABLE 1

| Preparation | Zone persistence (days) | Remarks |
|---|---|---|
| A | 72 | no resistance seen |
| B | >190 | no resistance seen |
| C | >190 | Resistance seen from Days 24-27 onwards |

The simulation was repeated using plates seeded with the gram-negative bacterium *E coli*. The results were as follows:

TABLE 2

| Preparation | Zone persistence (days) | Remarks |
|---|---|---|
| A | 0 | |
| B | 160 | no resistance seen |
| C | 175 | resistance seen after 53 days |

MICs of Triclosan for resistant mutants were: *S. aureus* 125 mg/l (Inoculum 3.75 mg/l), *E. coli* 250 mg/l (Inoculum 16 mg/l).

Figure 2:
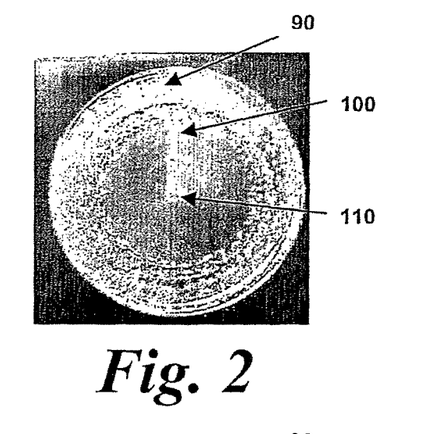
FIG. 2 schematically illustrates a plate of agar seeded with S aureus incubated with a silicone disc impregnated with rifampin, clindamycin and triclosan for 130 days and the disc then being removed.

FIG. 2 illustrates an agar plate 90 seeded with *Staphylococcus aureus* and incubated with a silicone disc impregnated with rifampin+clindamycin+triclosan for 130 days. The figure shows the plate 90 with the disc removed so that the presence of bacterial growth under the disc can be investigated. It can be seen from the figure that the site of the disc 110 has no visible bacterial growth and that there is a zone of inhibition 100 surrounding the site of the disc 110 in which there is no visible bacterial growth.

Figure 3:
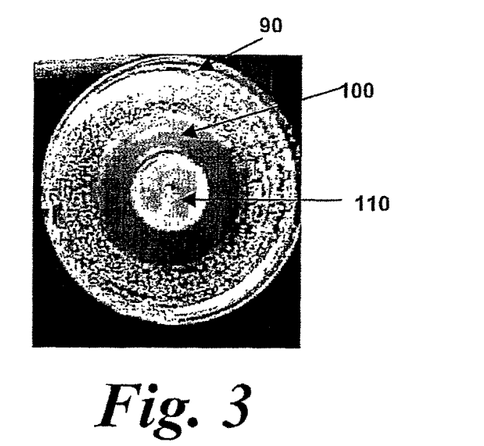
FIG. 3 schematically illustrates a plate of agar seeded with S aureus incubated with a silicone disc impregnated with triclosan alone for 130 days and the disc then being removed.

FIG. 3 illustrates an agar plate incubated under the same conditions as the plate illustrated in FIG. 2 except that the silicon disc is only impregnated with triclosan. It can be seen that there is a zone of inhibition around the site of the disc 110 but that there has been bacterial growth at the site of the disc 100 (i.e. under the disc). The bacteria found under the disc being resistant to triclosan (MIC on inoculum 3.75 mg/l, MIC of resistant mutants 125 mg/l).

Figure 4:
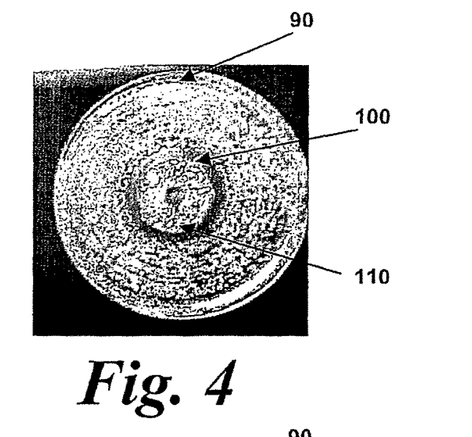
FIG. 4 shows a plate of agar seeded with S aureus incubated with a polyurethane foam disc impregnated with chlorhexidine alone for 130 days and the disc then being removed.

FIG. 4 illustrates an agar plate 90 seeded with *Staphylococcus aureus* and incubated with a polyurethane foam disc impregnated with chlorhexidine for 130 days. Such an impregnated disc is employed for prior art wound guards. The figure shows the plate 90 with the disc removed so that the presence of bacterial growth under the disc can be investigated. It can be seen that there is a zone of inhibition 100 around the site of the 110 the disc but this zone 100 is much smaller than that produced in the plates illustrated in FIGS. 2 and 3. There was bacterial growth at the site of the disc 100 (i.e. under the disc). The bacteria found under the disc 100 being resistant to chlorhexidine.

Figure 5:
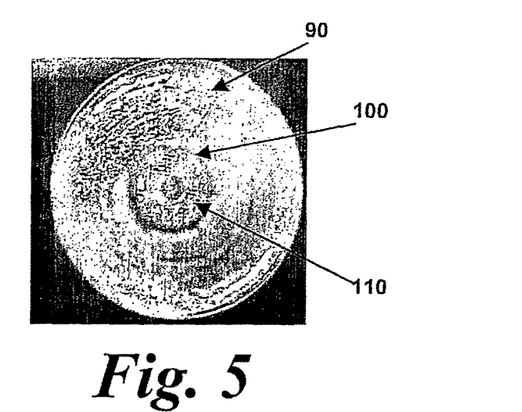
FIG. 5 shows a plate of agar seeded with E coli incubated with a polyurethane foam disc impregnated with chlorhexidine alone for 130 days and the disc then being removed.

FIG. 5 illustrates an agar plate incubated under the same conditions as that illustrated in FIG. 4 except that the agar is seeded with *E coli*. It can be seen that there is a zone of inhibition 100 around the site of the 110 the disc but this zone 100 is much smaller than that produced in the plates illustrated in FIGS. 2 and 3. There was bacterial growth at the site of the disc 100 (i.e. under the disc). The bacteria found under the disc being resistant to chlorhexidine.

Figure 6:
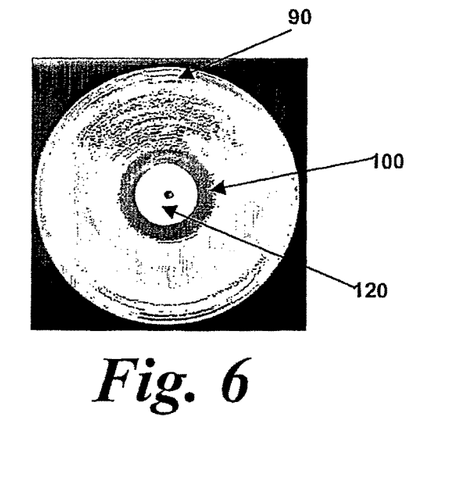
FIG. 6 shows a plate of agar seeded with E colt and a silicone disc impregnated with triclosan alone for 130 days.

FIG. 6 illustrates an agar plate seeded with *E coli* and incubated for 130 days with a silicone disc 120 that is impregnated with triclosan. It can be seen that there is a zone of inhibition 110 around the disc but that the zone is smaller than the zone exhibited in the plates illustrated in FIGS. 2 and 3.

Figure 7:
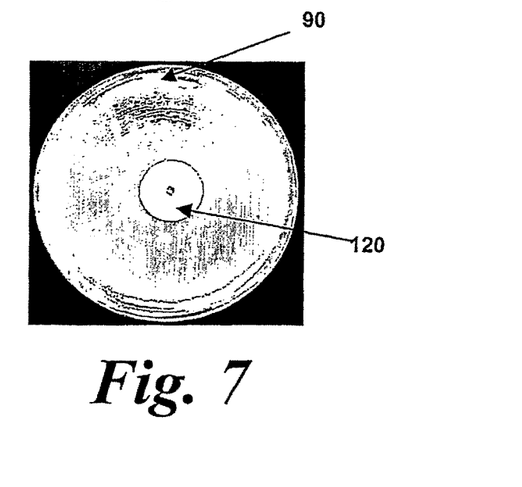
FIG. 7 shows a plate of agar seeded with E coli incubated with a silicone disc impregnated with triclosan alone for 130 days.

FIG. 7 illustrates an agar plate 90 seeded with E colt taken from under the disc 120 of the plate 90 illustrated in FIG. 6 (i.e. bacteria previously exposed to triclosan) and incubated for 130 days with a silicone disc 120 that is impregnated with triclosan. It can be seen that there is no zone of inhibition 110 around the disc 120 indicating that the bacteria taken from under the disc 120 in plate 90 illustrated in FIG. 6 have mutated to be resistant to triclosan.

Neither rifampin, clindamycin nor the combination of rifampin with clindamycin have growth-inhibitory activity against gram-negative bacteria such as *E coli*. Triclosan, used as a single antimicrobial agent, has a long activity against *E coli* but does not prevent resistant *E coli* strains forming. Therefore, it is surprising that the combination of triclosan, rifampin and clindamycin shows both long activity and inhibition of the appearance of mutant strains of *E coli*.

Triclosan has a long activity against a range microbes and, in particular, triclosan has long activity against *S aureus*. If triclosan is used in combination with other antimicrobial agents then no selection of resistance mutations is seen. The activity of the triclosan is not adversely affected by use as a combination with other drugs. This means that the combination of triclosan with one or more other agents is effective against infection for in excess of 190 days both in terms of providing antimicrobial activity and in preventing the appearance of resistant mutant strains.

Simulation of Catheter Track Protection

Figure 8:
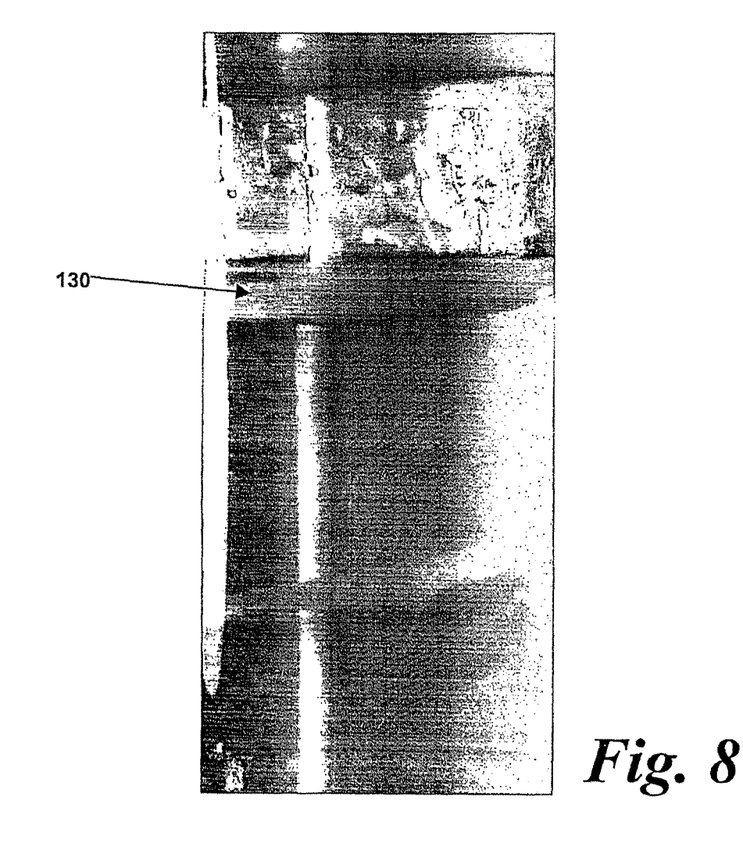
FIG. 8 shows a control catheter placed in semisolid agar.
Figure 9:
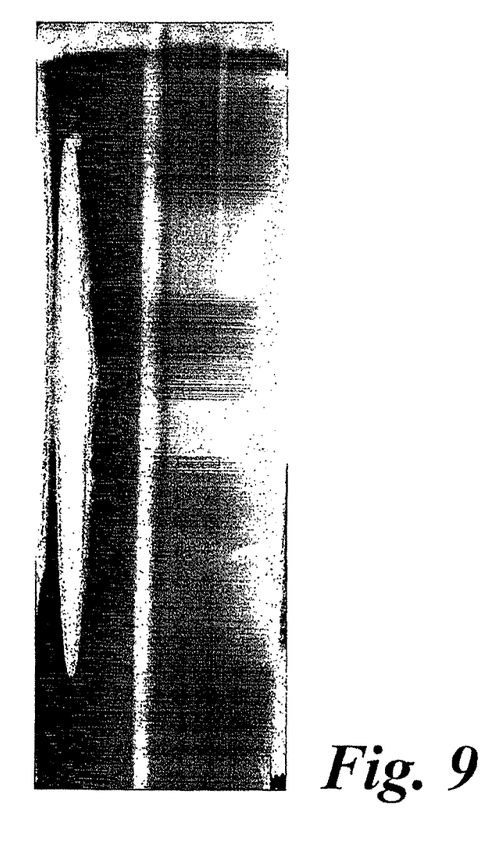
FIG. 9 shows a catheter impregnated with rifampin+clindamycin+triclosan placed in semisolid agar.

In a simulation of a catheter exit site/track infection, a catheter impregnated with rifampin+clindamycin+triclosan was inserted into simulated "tissue" (semisolid agar containing general bacterial nutrients plus dextrose and a pH indicator) and the "skin" exit site challenged daily with staphylococci. Unimpregnated catheters were used as a control (FIG. 8). For the unimpregnated catheters bacterial growth 130 was visible at the liquid/air interface and following the exterior surface of the catheter. The bacterial growth 130 changed the colour of the agar from purple to yellow indicating a fall in pH due to formation of acid metabolites. In contrast, the impregnated catheter (FIG. 9) showed no evidence of bacterial growth at the exit site and none could be seen tracking down the outside of the catheter. Nor was the pH changed (original colour purple).

Triclosan is neurotoxic and therefore should not come into contact with tissue comprising the central nervous system. Therefore, triclosan can be used to impregnate the distal end of an EVD and other antimicrobial agents such as rifampin and clindamycin can be used for the sub dermal portion of the EVD. A problem with such an impregnated EVD is that the triclosan can migrate from the distal end of the EVD to the sub dermal portion of the EVD. In an attempt to prevent such migration, a medical device may be made up of two separate portions, each having a different antimicrobial agent, the separate portions are then butted together. However it is possible that the antimicrobial agents can migrate through the butt joint. Attempts to solve this problem include placing a barrier between the two separate portions. From a regulatory point of view, the risks are that an agent such as triclosan, released into a catheter lumen, cannot be reasonably prevented from refluxing into the central nervous system (or at least there is a realistic risk). In order to circumvent this, the triclosan can be applied as an additional device, or "collar", around the outside of the catheter at the skin exit site. An alternative is to impregnate a portion of the collecting set well away from the patient and distal to the "non-return" apparatus (valve or drip chamber) that is intended to prevent reflux from the collecting bag.

Although, the diffusion of antimicrobial agents through silicone (or other polymers) can be seen as a problem we have realised, surprisingly, that an embodiment of the invention turns the diffusion effect to advantage to solve a problem encountered when trying to impregnate two different types of antimicrobial agent into a polymeric material using a different technique for each type of antimicrobial agent. The impregnation of one type of antimicrobial into a polymeric material may require conditions that are so severe that the other type antimicrobial agent (e.g. an organic antimicrobial compound) that is required in the polymeric material is destroyed or impaired. For example the impregnation of metals such as silver or copper into polymeric material requires the use of supercritical fluids, for example supercritical carbon dioxide, as a carrier so that metal atoms can be carried into the polymer matrix. The use of techniques involving super critical fluids may destroy or degrade organic, or non-metallic antimicrobial agents. Antibiotics can be impregnated into polymers using supercritical carbon dioxide but a concern is that the organometallic carriers of the antibiotics will degrade the antibiotics.

A solution to this problem according to an embodiment of the invention is to apply one technique to one piece of polymeric material, e.g. impregnating the polymeric material with silver using supercritical carbon dioxide, and apply a different technique to a different, separate piece 51 of polymeric material, e.g. impregnating the polymeric material with triclosan using the method illustrated in FIG. 1. In this way the process involved in one of the techniques will not deleteriously affect the antimicrobial agent used in the other technique.

The two pieces of polymeric material are then butted together. The two pieces may be joined together using polymer glue. When rifampin, clindamycin are used as antimicrobial agents in the silicone they have a tendency to migrate through the glue. Alternatively, the two pieces may be held together under compression or the two pieces may be shaped so a dovetail or other mechanical joint holds the two pieces together. Diffusion will then occur with the antimicrobial agent in each piece migrating to the other respective piece. Diffusion can be accelerated by several techniques including heating, autoclaving, and applying ultrasound to the polymeric material. Preferably, the diffusion is accelerated so that each antimicrobial agent is distributed, possibly evenly distributed, throughout the device, or at least throughout a region of the device, before the device is used.

Figure 19:
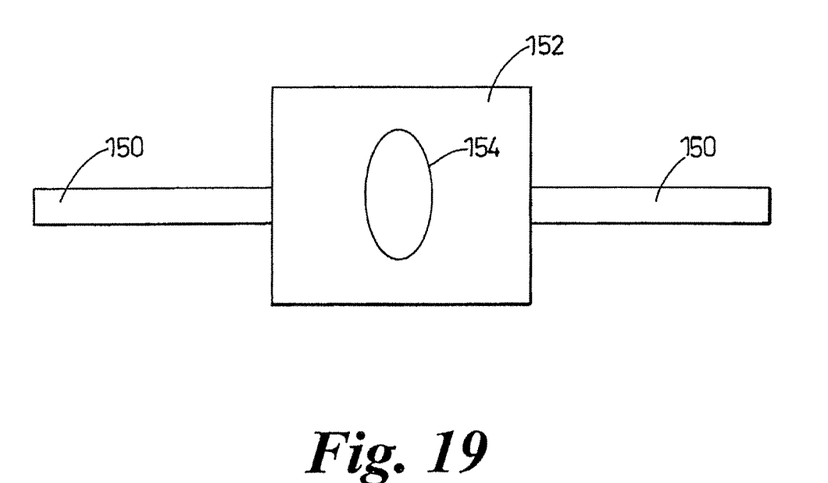
FIG. 19 schematically illustrates a medical device having a portion that can be subjected to impregnation with an antimicrobial agent according to the method illustrated in FIG. 1 and a further portion that is prone to damage if subjected to such an impregnation method.

Referring to FIG. 19, one or more portions 150 of a medical device (e.g. catheter portions) may be impregnated with one or more antimicrobial agents. A further portion 152 of the device may not be susceptible to impregnation because, for example, it comprises apparatus 154 that would be damaged or potentially damaged by the impregnation process (e.g. the impregnation process as described with reference to FIG. 1). To impregnate the further portion 152, the impregnated portions 150 can be joined or abutted to the further portion 152 and the antimicrobial agents in the impregnated portions 150 allowed to diffuse into the further portion 152. The diffusion can be accelerated by heating or autoclaving if such treatments are not detrimental to the apparatus 154.

Wound guards are used to protect the entry point of a transdermal device into the skin. Important examples of transdermal devices include central venous catheters, external ventricular drainage catheters, catheters for delivery of continuous ambulatory peritoneal dialysis (CAPD), and external fixation pins for fracture stabilisation.

Figure 10:
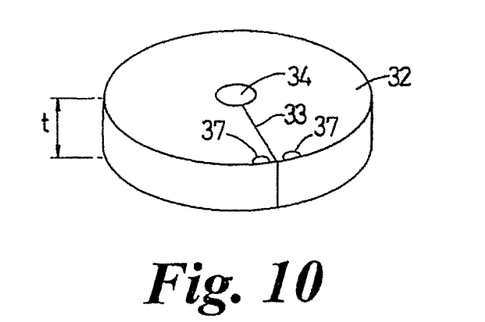
FIG. 10 schematically illustrates a first type of wound guard.
Figure 11:
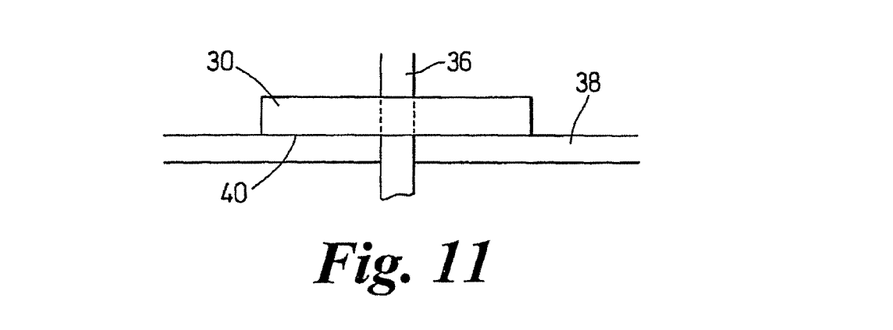
FIG. 11 schematically illustrates a cross-sectional view of the first type of wound guard when placed on the skin of a patient and supporting a transdermal device.
Figure 12:
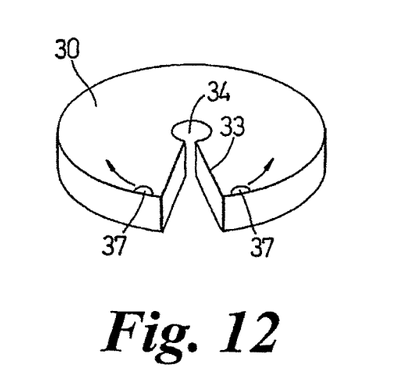
FIG. 12 schematically illustrates the first type of wound guard in which a slit in the wound guard has been opened for insertion or removal of a transdermal device.

Referring to FIGS. 10, 11 and 12, a first type of wound guard 30 is shown comprising a disc 32 of silicone elastomer having a central bore 34. The size of the bore 34 is chosen so that the transdermal device 36 may be placed through the bore 34 in a tight fit.

The wound guard 30 is positioned so that a surface 40 of the wound guard 30 abuts the skin 38 of the patient around the wound caused at the entry point of the transdermal device 36. The wound guard 30 protects the wound from exposure to microbes, dust, dirt or other contaminants that would infect or inflame the wound. The wound guard 30 is applied to the wound so that it exerts a slight downward pressure on the skin 38. This helps to keep the wound guard 30 in intimate contact with the skin if the patient moves. The downward pressure also acts to stop or reduce bleeding from the wound.

The disk 32 may have a radial slit 33, penetrating throughout the thickness of the disk 32 from the bore to the periphery of the disc, that allows the wound guard 30 to be to applied or removed from the transdermal device 36. In this case the disk 34 may also be provided with a protrusion 37 either side of the slit 33 so that a user may more easily part the slit 33 by applying outward pressure to the protrusions 37 with his or her fingers/thumbs.

For devices that transgress the dermal barrier a major risk of infection is at the skin exit site, which is colonised by commensal skin bacteria or which might become contaminated with more resistant strains of bacteria or enteric bacteria. Systemic antibiotics do not protect against, and tend to encourage, resistant strains of bacteria. To prevent infection, the wound guards 30 may be impregnated with one or more antimicrobial agents using, for example, the method illustrated in FIG. 1.

When the wound guard 30 is impregnated throughout with one or more antimicrobial agents a cut made to the wound guard 30 will expose a surface on which the one or more antimicrobial agents are present. This is in contrast to a wound guard that is merely coated with an antimicrobial agent.

Because the wound guard is composed of silicone elastomer it is non-absorbent for water and bodily fluids such as blood and plasma. This means that the wound guard 30 will not become soaked with blood or plasma from the wound and it is possible to wash the area of skin around the wound guard 30. It is also possible to remove the wound guard 30 from the wound and wash it (for example, to remove dried blood, dust etc.) and then replace it over the wound.

The surface 40 of the wound guard 30 that is in contact with the skin will generally be flat. The thicker the disc 32 the more rigid it becomes, if the disc is too rigid then it will not make good contact with the surface of the skin which will generally not be flat. Preferably, the disc should be thin enough so that it has sufficient flexibility to deform to make good contact with the skin around the wound when the wound guard 30 is applied. It is also desirable that the disc 32 has sufficient flexibility so that movement of the patient does not cause the disc 32 of the wound guard 30 to dig into the patients skin. The thickness of the disc 30 that can be used depends on the size of the disc 32—larger discs will need to be thinner than smaller discs. For example, a silicone disc 32 that has a diameter of about 2.5 cm generally has a thickness in the range 1.0-4.0 mm. Silicone elastomer is a good choice of material for the wound guard because it has the appropriate elasticity and flexibility to allow the wound guard to deform to suit the wound site whilst applying downward pressure on the wound.

Generally a wound guard 30 made of silicone elastomer will be transparent. This enables inspection of the wound site without the need to remove the wound guard 30.

Instead of a silicone elastomer a different polymeric material, that has broadly similar properties of non-absorbance of bodily fluids, flexibility and tear resistance, could be used.

Figure 13:
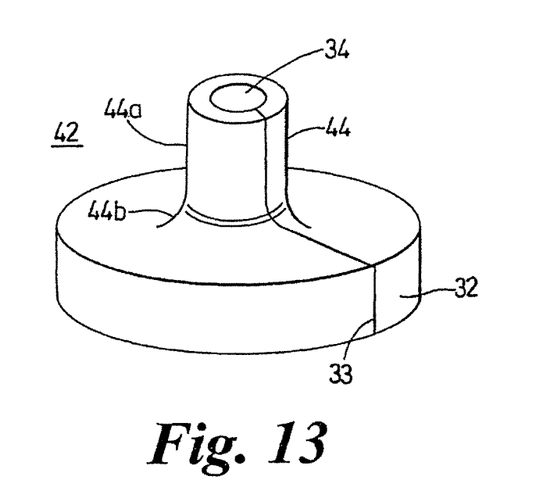
FIG. 13 schematically illustrates a second type of wound guard.
Figure 14:
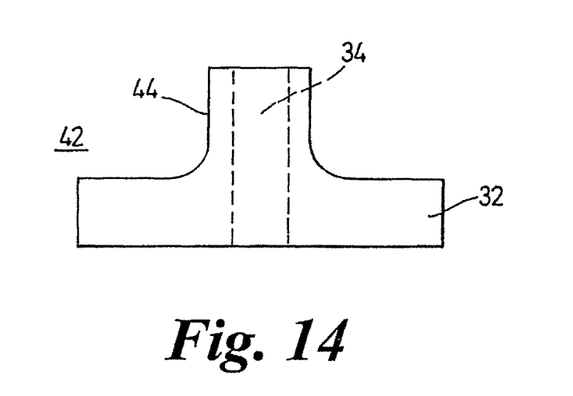
FIG. 14 schematically illustrates a cross-sectional view of the second type of wound guard.

With reference to FIGS. 13 and 14, a second type of wound guard 42 has a disc portion 32 and a projection 44 from the disc portion 32. The disc portion 32 may be similar to the disc portion 32 of the first type of wound guard 30 and may have the same features as described with reference to the first type of wound guard 32. The projection protrudes from the opposite surface of the disc 32 than the surface 40 that is for contact with the patient's skin 38. For the second type of wound guard 42 the bore 34 passes through both the disc portion 32 and the protrusion 44. The second type of wound guard 42 may also have a radial split 33 penetrating throughout the thickness of the wound guard 42 (i.e. through the disc portion 32 and the projection 44) from the bore to the periphery of the wound guard 42, that allows the wound guard 42 to be easily applied or removed from the transdermal device 36.

Figure 15:
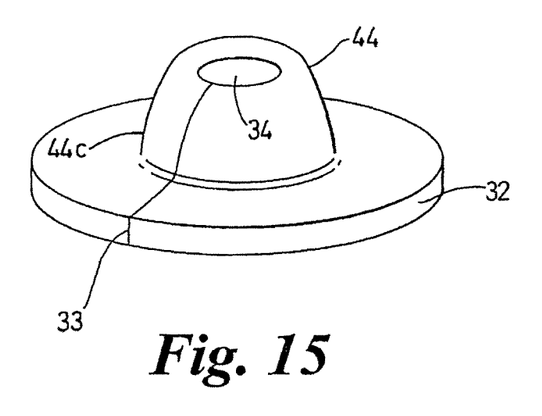
FIG. 15 schematically illustrates a further example of the second type of wound guard.
Figure 16:
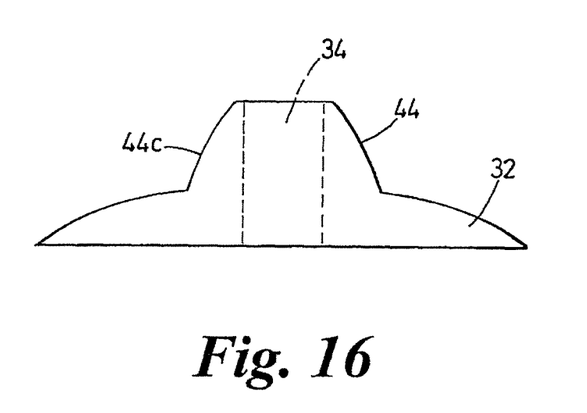
FIG. 16 schematically illustrates a cross-sectional view of the further example of the second type of wound guard.

The wound guard 42 illustrated in FIGS. 13 and 14 has a projection 44 that has a cylindrical portion 44a distal from the disc portion and a concave portion 44b proximal to the disc portion 32. The projection 44 may also be shaped so that there is no cylindrical portion 49a and the concave portion 44b, in this case, would extend from the disc portion to the end of the projection that has the bore 34 entrance. Referring to FIGS. 15 and 16, instead of a concave portion 44b the projection 44 may have a convex portion 44c. FIGS. 10 and 11 show the convex portion 44c extending from the disc portion 32 to the end of the projection 44 that has the bore 34 entrance but the projection 44 may also be shaped so that it has a distal cylindrical portion 44a. The projections with such shapes provide a large surface area for the junction between the projection 44 and the disc portion 32 whilst having a smaller plan area for the portion of the projection 44 that is distal from the disc portion 32. The skilled person may envisage other geometries that achieve this function, e.g. a projection 44 that is frusto-conical.

Referring to FIG. 16, the disc portion 11 may be thinner at its periphery than at its centre. Such geometry provides the disc portion 32 with enhanced flexibility.

The second type of wound guard 42 may be impregnated with one or more antimicrobial agents in a similar way to the first type of wound guard 30. The disc portion 32 should at least be impregnated and preferably the protrusion 44 should also be impregnated.

Preferably, the second type of wound guard is made of silicone elastomer, but it could be made of other polymeric materials.

The purpose of the protrusion 44 is to provide an increased length of bore 34 so that there is more contact between the wound guard 42 and the device 36. The increased contact provides increased frictional resistance to movement of the device 36 within the bore 34 and gives more longitudinal support to the device 36, and also more lateral, transverse, mechanical support.

The height of the protrusion 44 above the disc is generally in the range 15 to 25 mm. The second type of wound guard 42 is not unduly rigid because the extra thickness of the second type of wound guard 42, due to the height of the protrusion 44, is over only a limited part of the disc portion 32 of the wound guard 42, i.e., the extra thickness is only for the area around the bore 34 through which the device 36 passes.

Because the wound guard 42 is made of silicone elastomer it will grip the device passing through the bore 34 of the wound guard. The transdermal device 36 will be gripped by a wound guard 30 that only has a disc portion but a wound guard 42 that also has a protrusion 34 will have an increased grip on the device 34. Because the wound guard 42 grips the device 34, e.g. a catheter, the wound guard 42 can be securely positioned over a patient's wound by appropriately positioning the wound guard 42 on the device 34. In this way it is not necessary to use adhesive between the skin 38 of the patient and the underside 40 of the wound guard 42, although adhesive could be used if desired.

Generally the protrusion 44 (including the cross-sectional area of the bore) will have a plan area that is less than 20% of the plan area of the disc portion 32. Preferably the protrusion 44 is less than 15%, 10% or 5% of the plan area of the disc portion 32.

The protrusion 44 is generally cylindrical. The protrusion 44, therefore, can be considered to act as a collar, boss, flange or spigot. The shape of the cross-section of the protrusion 42 is not important but it may be convenient to form a protrusion 42 that has a circular cross-section, i.e. the protrusion 42 is annular. The protrusion 44 may be integral with the disc portion 32, for example the protrusion 44 and disc portion 32 may be formed from the silicone elastomer in the same operation. Alternatively, the protrusion 44 and disc portion 32 may be made separately and then bonded together.

Figure 17:
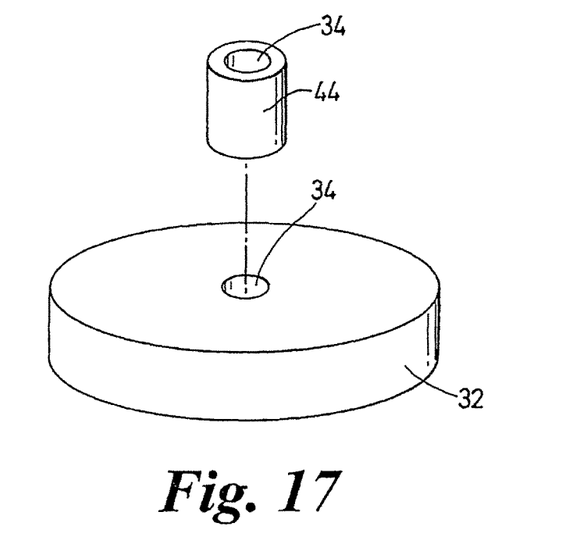
FIG. 17 schematically illustrates a version of the second type of wound guard having a separable projection portion.
Figure 18:
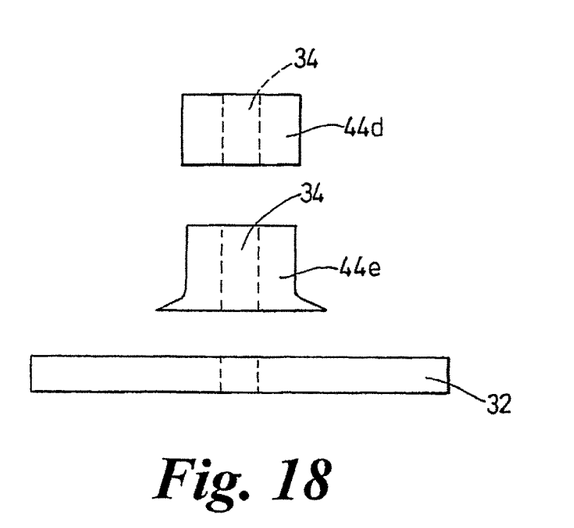
FIG. 18 schematically illustrates a version of the second type of wound guard having a separable projection portion which is made up of two separable parts.

Referring to FIGS. 17 and 18, the protrusion 44 may not be integral with the disc portion 32. In this case the device 36 is placed through a bore in the disc portion 32 and a bore in the protrusion 44 so that the protrusion 26 abuts the disc portion 32. This allows for the protrusion 44 to have a large height above the disc portion 32 whilst still allowing the disc 32 to flex. As illustrated in FIG. 18 the protrusion may comprise two or more separable portions 44d, 44e.

It will be appreciated that the medical devices described herein are applicable for use with animals as well as human patients and may be used in veterinary practice to treat cats, dogs, horses, rabbits and the like.

It will also be appreciated that the various features described in the specification, or as set out in the claims, can be used in any combination with each other.

The invention claimed is:

1. A medical device material consisting of a polymeric material impregnated with a first antimicrobial agent being triclosan, a second antimicrobial agent being rifampin, and a third antimicrobial agent being clindamycin, wherein the concentration of triclosan in the polymeric material is between 0.1% and 3% w/w in comparison to the weight of the polymeric material, the concentration of the second antimicrobial agent in the polymeric material is 0.05 mg/g in comparison to the weight of the polymeric material, the concentration of the third antimicrobial agent in the polymeric material is 0.16 mg/g in comparison to the weight of the polymeric material and wherein the medical device material provides antimicrobial activity and inhibition of resistant microbial mutations for 80 days or more for both gram-positive and gram-negative bacteria.

2. The medical device material of claim 1, wherein the gram-negative bacteria includes Escherichia coli and wherein the gram-positive bacteria includes Staphylococcus aureus.

3. The medical device material of claim 1, wherein the polymeric material is selected from the group consisting of silicone elastomer, a polyalkene, polyethylene terephthalate, polyvinyl chloride, polytetrafluoroethylene (PTFE), silicone polyurethane copolymer and polyurethane latex.

4. The medical device material of claim 1, wherein the medical device material provides antimicrobial activity and inhibition of resistant microbial mutations for 90 days or more.

5. The medical device material of claim 1, wherein the medical device material provides antimicrobial activity and inhibition of resistant microbial mutations for 100 days or more.

6. The medical device material of claim 1, wherein the medical device material provides antimicrobial activity and inhibition of resistant microbial mutations for 120 days or more.

7. The medical device material of claim 1, wherein the medical device material provides antimicrobial activity and inhibition of resistant microbial mutations for 140 days or more.

8. The medical device material of claim 1, wherein the medical device material provides antimicrobial activity and inhibition of resistant microbial mutations for 160 days or more.

9. The medical device material of claim 1, wherein the medical device material provides antimicrobial activity and inhibition of resistant microbial mutations for 190 days or more.

10. A medical device comprising a medical device material consisting of a polymeric material impregnated with a first antimicrobial agent being triclosan, a second antimicrobial agent being rifampin, and a third antimicrobial agent being clindamycin, wherein the concentration of triclosan in the polymeric material is between 0.1% and 3% w/w in comparison to the weight of the polymeric material, the concentration of the second antimicrobial agent in the polymeric material is 0.05 mg/g in comparison to the weight of the polymeric material, the concentration of the third antimicrobial agent in the polymeric material is 0.16 mg/g in comparison to the weight of the polymeric material and wherein the medical device material provides antimicrobial activity and inhibition of resistant microbial mutations for 80 days or more for both gram-positive and gram-negative bacteria.

11. The medical device of claim 10, wherein the gram-negative bacteria includes Escherichia coli, and wherein the gram-positive bacteria includes Staphylococcus aureus.

12. The medical device of claim 10, wherein the medical device provides antimicrobial activity and inhibition of resistant microbial mutations for 90 days or more.

13. The medical device of claim 10, wherein the medical device provides antimicrobial activity and inhibition of resistant microbial mutations for 100 days or more.

14. The medical device of claim 10, wherein the medical device provides antimicrobial activity and inhibition of resistant microbial mutations for 120 days or more.

15. The medical device of claim 10, wherein the medical device provides antimicrobial activity and inhibition of resistant microbial mutations for 140 days or more.

16. The medical device of claim 10, wherein the medical device provides antimicrobial activity and inhibition of resistant microbial mutations for 160 days or more.

17. The medical device of claim 10, wherein the medical device provides antimicrobial activity and inhibition of resistant microbial mutations for 190 days or more.

18. The medical device of claim 10, wherein the polymeric material is selected from the group consisting of silicone elastomer, a polyalkene, polyethylene terephthalate, polyvinyl chloride, polytetrafluoroethylene (PTFE), silicone polyurethane copolymer and polyurethane latex.

19. The medical device of claim 10, wherein the medical device is selected from the group consisting of: an external ventricular drainage device, an ommaya reservoir, an intraspinal pump, a central venous catheter, an ascites shunt, a pacemaker, a continuous ambulatory peritoneal catheter, a voice prosthesis, a vascular graft, a urinary catheter, an intraocular lens and a wound guard.

20. The medical device of claim 10, which has a transdermal portion.

21. The medical device of claim 19, wherein the device comprises a urinary catheter.

22. The medical device of claim 10, wherein the medical device is a continuous ambulatory peritoneal dialysis catheter.

* * * * *